United States Patent [19]

Dickakian

[11] Patent Number: 4,751,187

[45] Date of Patent: Jun. 14, 1988

[54] CHROMATOGRAPHIC METHOD FOR DETERMINING FOULING TENDENCY OF LIQUID HYDROCARBONS

[75] Inventor: Ghazi B. Dickakian, Kingwood, Tex.

[73] Assignee: Exxon Chemical Patents Inc., Linden, N.J.

[21] Appl. No.: 723,598

[22] Filed: Apr. 15, 1985

[51] Int. Cl.$^4$ .............................................. G01N 30/90
[52] U.S. Cl. .................... 436/60; 73/61.1 C; 73/61.2; 208/48 AA; 208/309; 436/139; 436/162
[58] Field of Search ................ 436/161, 162, 139, 60; 208/48 AA, 309; 73/61.2, 64, 61 R, 54, 61.1 C

[56] References Cited

U.S. PATENT DOCUMENTS

| | | | |
|---|---|---|---|
| 1,756,981 | 5/1930 | Jurrissen | 208/309 X |
| 2,196,989 | 4/1940 | Henry et al. | 208/309 X |
| 2,927,078 | 3/1980 | Nathan | 208/48 AA X |
| 2,981,684 | 4/1961 | Barnes | 208/48 AA X |
| 3,049,964 | 8/1962 | Miller et al. | 73/64 U X |
| 3,776,835 | 12/1973 | Dvoracek | 208/48 AA |
| 4,440,625 | 4/1984 | Go et al. | 208/48 AA |

FOREIGN PATENT DOCUMENTS 455272  4/1975  U.S.S.R. ................................. 73/64

OTHER PUBLICATIONS

Poirier et al., Chemical Abstracts, vol. 100, 1983, No. 100:36717m.
Poirier et al., Energy Sources, vol. 7, No. 2, pp. 165-176, 1983.
Touchstone et al., "Practice of Thin Layer Chromatography", Published by John Wiley & Sons, New York, pp. 135-141, 1978.

*Primary Examiner*—Barry S. Richman
*Assistant Examiner*—Robert J. Hill, Jr.
*Attorney, Agent, or Firm*—R. L. Graham; J. F. Hunt

[57] ABSTRACT

A method for determining the fouling tendency of an asphaltene containing hydrocarbon stream such as crude oil by the use of thin layer chromatography. The chromatogram of a crude oil exhibiting a fouling tendency developed a distinct, dark ring or disk.

7 Claims, 4 Drawing Sheets

CRUDE (BT)
(HIGH FOULING)

BT DISTILLATE
(NO FOULING)

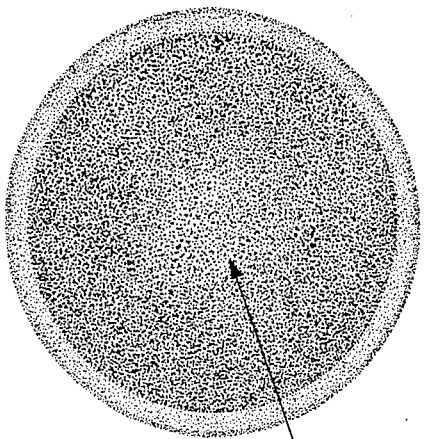
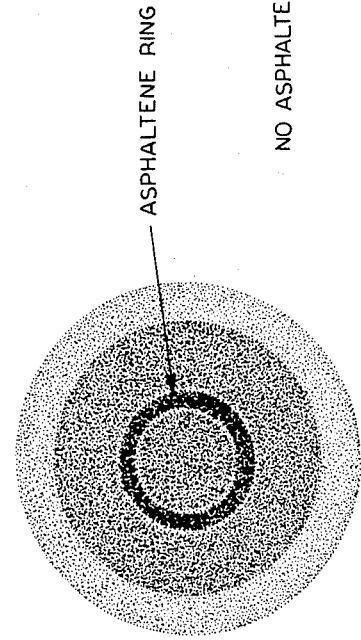
FIG. 4

CHROMATOGRAPHIC METHOD FOR DETERMINING FOULING TENDENCY OF LIQUID HYDROCARBONS

FIELD OF THE INVENTION

The present invention relates to a test method for determining the tendency of liquid hydrocarbon streams to foul equipment and more particularly to a method for determining oil-asphaltenes incompatibility and related fouling tendency.

BACKGROUND OF THE INVENTION

Different asphaltenes containing hydrocarbon streams have different precipitating and fouling characteristics with regard to heated oil refinery surfaces. The problem of predicting the offending substances in a particular stream such as crude oil which foul heat-exchanger equipment in oil refineries and petrochemical plants has been virtually unresolved. Equipment fouling by heated hydrocarbon streams which results in carbonaceous deposits on heat-exchanger surfaces leads to a blockage of flow and a decrease in heat transfer. Both resulting conditions severely reduce heat efficiency in the processing of the crude oil. If it can be predicted which crude oils are troublesome, measures can be taken in advance to prevent this fouling by either removing the offending substances causing the deleterious deposits, or by adding antifouling additives to the flow stream to reduce depost formation. Therefore, it would be most desirable to be able to predict these streams with fouling tendencies.

There are a number of methods available for determining the rates of fouling of hydrocarbon streams. Conceptually, they are all similar in that they attempt to measure the change in heat transfer from a heated surface to a test fluid.

One approach is to use a test unit which is configured to allow measurement of the fluid temperature at the exit of the heat-exchanger while the metal temperature of the heated tube is controlled. This configuration provides for close simulation of refinery and petrochemical plant heat-exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature, while measuring the change in the liquid outlet temperature. As fouling progresses, i.e., a carbonaceous deposit build up on the heater tube surface, a decrease in the fluid outlet temperature results when using a constant outlet liquid temperature operation. The change in liquid outlet temperature with time provides the basic heat data required for comparative evaluation of untreated material and additive-treated material. The rate of change in outlet liquid temperature versus time shows relative fouling tendencies.

Present test equipment is only capable of measuring the overall tendency of heated hydrocarbon streams to foul refinery equipment and cannot predict which are the offending substances or fractions.

It is an object of this invention to provide a method which will predict the fouling tendency of asphaltene containing hydrocarbon streams such as residual and crude oils. These and other objects of the invention will be apparent from the following text.

SUMMARY OF INVENTION

Figure 1:
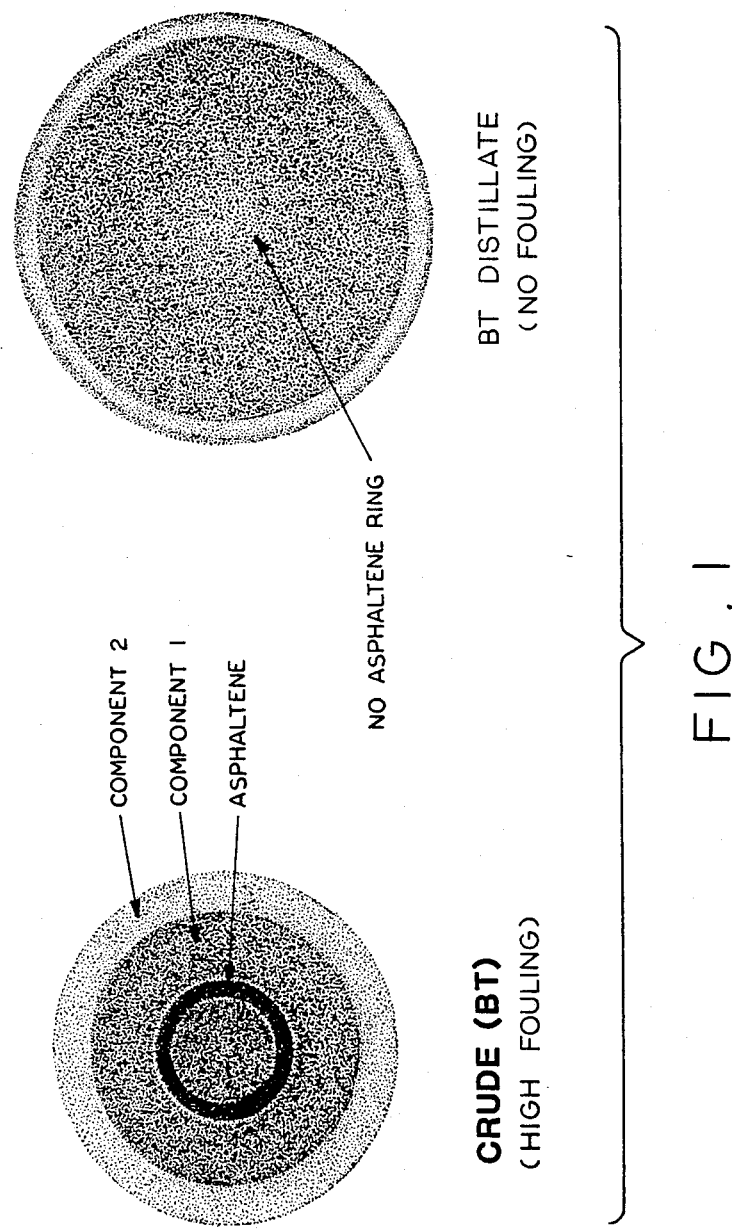
FIG. 1 illustrates chromatograms of a high fouling crude oil designated Crude (BT) and its distilled component.

The objects of this invention have been met by a method for determining the tendency of a liquid hydrocarbon stream containing asphaltenes to foul refinery equipment comprising the steps of:

depositing a small amount, e.g. one drop, of liquid hydrocarbon from said stream onto the surface of a thin film having the property of chromatographic separation;

providing sufficient time for outward migration within said film of said amount; and, determining the presence of an asphaltene ring in the thin film whereby the hydrocarbon-asphaltenes incompatibility is evidenced.

Thus, there has been discovered an effective, simple, inexpensive tool for visually identifying the fouling tendency of asphaltene containing liquid hydrocarbon streams. This discovery is based on a recognition of the asphaltenes-oil incompatibility of hydrocarbons streams possessing high fouling tendencies.

The utility of this discovery is demonstrated according to this invention by the use of thin layer chromatography as a means to determine the incompatibility of the high molecular weight asphaltene and oil fractions of the hydrocarbon stream.

Thus, there is provided a method for determining the tendency of oil containing asphaltenes to foul refinery equipment comprising the step of chromatographically separating said oil within a medium into respective light fractions and asphaltenes, whereby said tendency of said crude oil to foul said refinery equipment is visually indicated by a distinct demarcation between light fractions and said asphaltenes fraction.

DETAILED DESCRIPTION OF THE INVENTION

Hydrocarbon streams used in refinery operations, in particular, crude oils, are composed of two major parts; high molecular weight asphaltene (fraction insolubles in paraffinic solvents) and a lower molecular weight asphaltene-free oil. The asphaltene and the oil fraction vary significantly in their chemical structure, coking characteristics, thermal characteristics, average molcular weight and distribution. The following Table 1 illustrates the varying differences in the characteristics of a typical heavy hydrocarbon, its asphaltene and oil fractions:

TABLE I

|  | Total Hydrocarbon | Oil | $C_7$-Asphaltenes |
|---|---|---|---|
| Aromatic Rings | 3 to 7+ | 3,4,5 | 7+ |
| Average mol. wt. | 250 | 190 | 800 |
| Coking yield (wt. %) | 8 | 3 | 65 |
| Aromatic carbon (atom %) | 65 | 60 | 69 |
| Carbon Hydrogen atomic ratio | 0.97 | 0.90 | 1.19 |
| Melting point (°C.) | liquid | liquid | 190 |

Asphaltenes present in heavy hydrocarbons have high molecular weight and very broad molecular weight distribution, sometimes with molecular weights up to 10,000.

Generally speaking, the invention uses Thin Layer Chromatography (TLC) to separate, e.g., by adsorption, the high molecular weight asphaltenes and and the low molecular weight crude oil fractions. Thin layer chromatography is a well known technique as described in a book by Joseph C. Touchstone and M. F. Dobbins, entitled: "Practice of Thin Layer Chromatography," published by Wiley-Interscience, 1978.

Thin layer chromatography is a separation method in which uniform thin layers of selected sorbent media are used as a carrier medium. The sorbent is applied to a backing as a coating to obtain a stable layer of suitable size. The most common support is a glass plate, but other supports such as plastic sheets and aluminum foil are also used. The four sorbents most commonly used are silica gel, alumina, kieselguhr (diatomaceous earth), and cellulose. Silica gel (silicic acid) is the most popular material. It is slightly acidic in nature. In order to hold the silica gel firmly on the support, a binding agent such as plaster of paris (calcium sulfate hemihydrate) is commonly used. Separation can be accomplished in less than an hour at a very reasonable cost.

Fouling tendencies of the crude oil are indicated in the chromatographic medium by extreme differences in the migration of the molecularly light and heavy fractions. These differences are shown by a clear demarcation between visually light and dark areas. Where heavy asphaltene fractions are incompatible with the lighter matrix oil, a distinct dark colored ring or disk is formed as a result of the outward migration of the crude oil from the point of its deposition onto the chromatographic medium.

The invention features a method for predicting the fouling tendency of a crude oil to foul refinery equipment using the TLC techniques with a specific absorbent medium.

The crude oil is separated in a thin sorbent medium into respective molecularly light and heavy (asphaltenes) fractions, which are characterized by visually light and dark areas within the medium. The tendency of the crude oil to cause fouling in the refinery equipment is indicated by a visually distinct demarcation between the light and dark areas which dark area appears as a ring or disk.

A drop of the hydrocarbon stream to be tested is deposited on and thereby introduced into the thin layer chromatographic medium and fractionated by allowing the various fractions to migrate for a time sufficient to produce distinct demarcations between them. As previously discussed, the formation of a dark brown or black ring in the center of the medium will indicate the presence of incompatible high molecular weight asphaltenes which will have a tendency to cause fouling in conventional oil refinery operations.

Presently used methods, procedures and equipment are only capable of measuring the overall tendency of crude oils to foul refinery equipment, and cannot predict which offending substances or fractions are responsible for fouling. Such present test equipment accelerates the heat conditions leading to precipitation of carbonaceous deposits, without analyzing which fractions of the crude oil are responsible for the fouling.

The use of thin layer chromatography to separate the fractions of various fouling and non-fouling crude oils to identify the oil-asphaltene incompatibility provides a method capable of predicting by a quick and inexpensive test when a particular crude oil would foul the refinery equipment. This method of the invention can be corroborated by thereafter determining which crude oils have a tendency to cause fouling by the Thermal Fouling Tester (an apparatus widely used in the industry to measure the fouling tendencies of crude oils and other hydrocarbon streams). Chromatograms of the various crude oils have been made, and the results of these chromatograms thereafter correlated to the known fouling characteristics of each crude oil.

All of the Examples cited herein demonstrating the predictability of the fouling characteristics of crude oils utilized for corroboration of the prediction of this laboratory test apparatus known as the Thermal Fouling Tester.

The Tester is a modification of the Alco Tester described in ASTM Vol. 50 D-3241. It is configured to allow measurement of the fluid temperature at the exit of the heat-exchanger while the metal temperature of the heated tube is controlled. The test thus measures the change in temperature of a fluid which has been pumped across a heated surface. The outlet temperature is directly related to the heat transferred to the fluid. If fouling occurs, a deposit adheres to the heated metal surface and insulates a portion of the surface from the test fluid. The insulating deposit reduces the rate of heat transfer to the fluid and its temperature decreases. The rate of change in the fluid temperature is a measure of the rate of fouling.

The time over which temperature measurements are recorded was set at 3 hours. By doing this, the changes in temperatures of several fluids can be used as a measure of their relative fouling tendencies.

As used herein, oil-asphaltene incompatibility of the total hydrocarbon stream is indicative of the susceptibility of asphaltenes to separate from the oil, adhere to the heated metal surface, transfer into coke-like material and result in fouling of the metal surface. The greater the incompatibility of the asphaltenes in the oil; the higher the fouling tendency of the hydrocarbon stream.

In some circumstances, it may be useful to enhance the TLC separation of the asphaltenes from the oil fractions. This can be accomplished by dilution of the test sample of the hydrocarbon stream with a paraffinic solvent such as n-heptane, iso-octane and hexane. The dilution with solvent can be varied from 1 to 3,000 percent based on the weight of the test sample. The dilution is made prior to depositing the sample onto the TLC film.

Once the hydrocarbon stream has been identified as fouling according to the TLC method disclosed herein, it is desirable to reduce fouling by incorporating a small quantity of an antifouling agent (such as dispersants well known in the oil refining industry) into the hydrocarbon stream. Thus, in accordance with this invention there is provided a method for reducing the fouling tendency of hydrocarbon streams flowing through a vessel comprising the steps of:

(1) depositing a small amount of liquid hydrocarbon from said stream onto the surface of a thin film having the property of chromatographic separation;

(2) providing sufficient time for outward migration within said film of said amount;

(3) determining the presence of an asphaltenes ring in the thin film; and, (4) thereafter adding at least an antifouling amount of an antifouling agent to said stream whereby its tendency to foul is reduced.

The following Examples are reported for illustrative purposes only and are not to be construed as limiting the invention herein described.

Unless specified otherwise, as used herein, all parts and percentages are by weight and based on the total weight of the oil.

The various crude oils were subjected to thin layer chromatography according to the following examples, the respective fouling tendencies identified by use of the above-referenced Thermal Fouling Tester.

Chromatographic Separation of Hydrocarbon Streams

The following procedure was used in examples 1-4 to produce the several Thin Layer chromatograms.

A 10×10 cm silica gel coated glass plate was used. A drop of the crude oil or the fraction was dropped gently on the plate. The plate was allowed to stand at room temperature on a flat surface for from one minute to several hours. For light crude oils and fractions the separation was completed in a few minutes. For heavy crudes with very high viscosity such as SJV crude the separation required a few hours.

Figure 2:
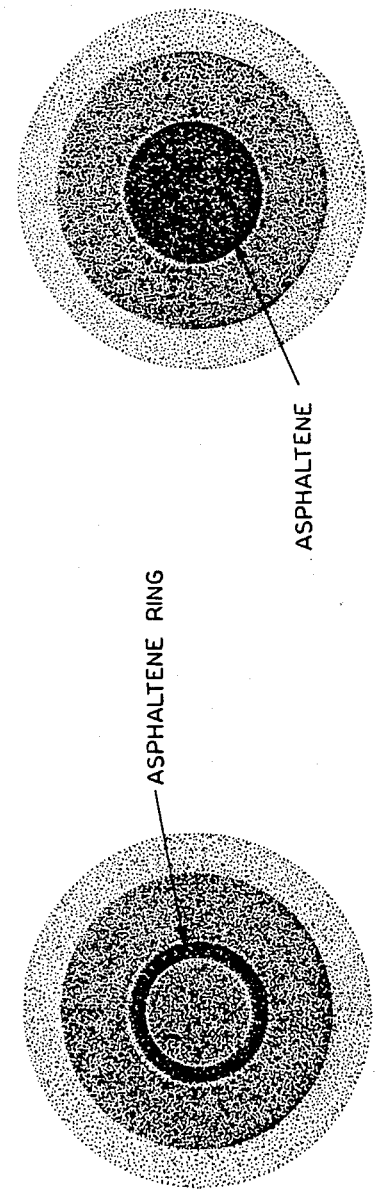
FIG. 2 illustrates chromatograms of a high fouling crude oil designated Crude (BT) and its asphaltenated crude modification.

The resulting chromatograms developed as a result of the placing of a drop of crude oil at the center of a silica gel film is illustrated in the drawings of FIGS. 1-4. The chromatograms illustrative of various types of crude oils are illustrated as follows:

FIG. 1 illustrates chromatograms of a high fouling crude oil designated Crude (BT) and its distilled component;

FIG. 2 illustrates chromatograms of a high fouling crude oil designated Crude (BT) and its asphaltenated crude modification.

Figure 3:
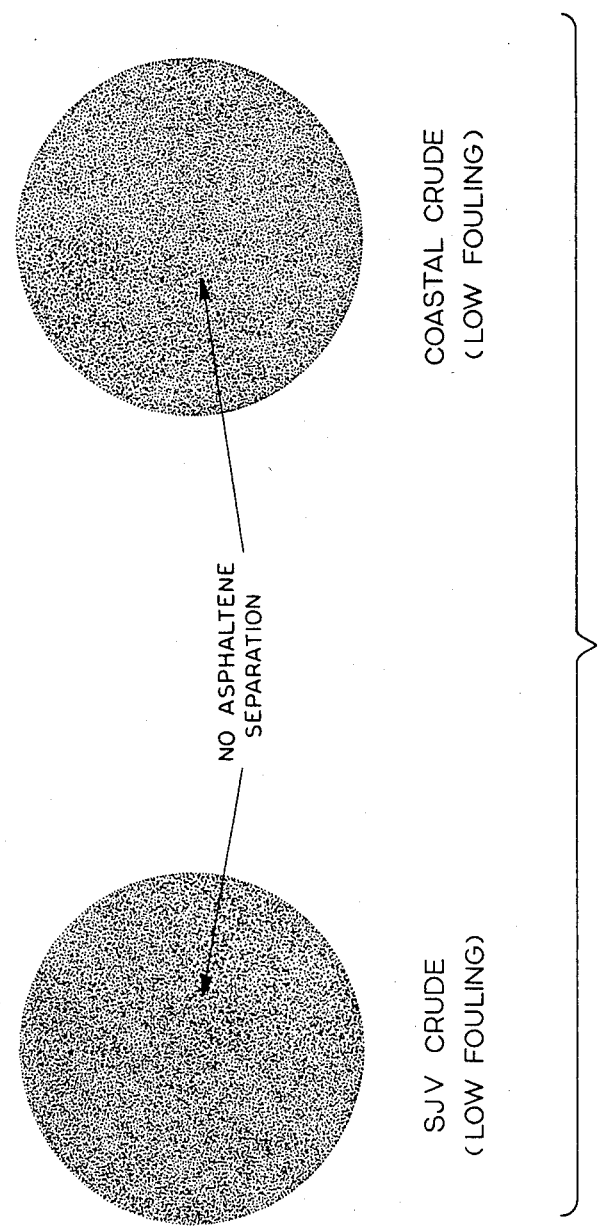
FIG. 3 illustrates chromatograms of two low fouling crude oils designated Coastal Crude and SJV Crude; and, FIG. 4 illustrates the chromatograms of the high fouling crude oil, Crude (BT) of FIG. 1 and its asphaltene-free (deasphaltenated) crude modification, Deasphaltenated Crude (BT).

FIG. 3 illustrates chromatograms of two low fouling crude oils designated Coastal Crude and SJV Crude; and, FIG. 4 illustrates the chromatograms of the high fouling crude oil, Crude (BT) of FIG. 1 and its asphaltene-free (deasphaltenated) crude modification, Deasphaltenated Crude (BT).

EXAMPLE 1

A sample of high fouling crude oil, Crude (BT) and a light distillate of Crude (BT) were each subjected to chromatographic separation at room temperature. After about one minute each exhibited the respective chromatograms illustrated in FIG. 1.

The left diagrammatic view of FIG. 1 illustrates the TLC chromatogram of the asphaltene containing high fouling Crude (BT) showing distinctly the dark colored asphaltenes ring as a concentric ring in the chromatogram.

The right diagrammatic view of FIG. 1 illustrates the TLC chromatogram of an asphaltene-free distillate of Crude (BT). The chromatogram shows no presence of an asphaltene ring. This distillate of Crude (BT) shows no fouling tendency as measured by the Thermal Fouling Tester (TFT).

EXAMPLE 2

A sample of the high fouling crude oil, Crude (BT) was modified by the addition of about 5 weight percent of asphaltenes (derived from Crude [BT]) to provide the asphaltenated Crude modification referenced in the description of FIG. 2. The asphaltenated crude modification was subjected to chromatographic separation for one minute.

The left diagrammatic view of FIG. 2 is the same as illustrated in FIG. 1. The right diagrammatic view of FIG. 2 illustrates the increased area and intensity of the asphaltene ring resulting from a TLC chromatogram when asphaltenes are added to Crude (BT) to increase its fouling tendency. Note that the resulting ring appears as a disk.

EXAMPLE 3

Two non-fouling crude oils designated as SJV and Coastal Crude were each subjected to chromatographic separation for several hours at room temperature. The resulting chromatograms of each are illustrated in FIG. 3. As apparent from each chromatogram of FIG. 3, neither shows the presence of an asphaltenes ring or disk.

EXAMPLE 4

The high fouling crude oil of Example 1, Crude (BT) was deasphaltenated by centrifugation to remove the asphaltenes. The resulting deasphaltenated Crude (BT) was subjected to chromatographic separation for several minutes. The resulting chromatogram is illustrated as the right diagrammatic view of FIG. 4. This chromatogram showed no asphaltenes ring or disk. The TFT, as will be seen, corroborates the marked lowered fouling tendency of the deasphaltenated Crude (BT) relative to the fouling tendency of Crude (BT).

EXAMPLES 5-10

Fouling Measurement of Various Hydrocarbon Types by Thermal Fouling Tester.

The Thermal Fouling Test was used to determine the fouling characteristics of 3 crude oils, a crude distillate by distillation, asphaltenated crude oil (BT) and deasphaltenated crude oil (BT).

Thermal Fouling Unit tests were carried out for 180 minutes at the following operating conditions:

Tube temperature=371° C.
Nitrogen pressure=500 psig
Crude flow=3.0 ml/min.
Preheat time to 371° C.=20 min.
Inner heater tube=Reconditioned (Carbon/Steel)

A summary of the fouling characteristics ($\Delta T$, °F) of the several hydrocarbon types is presented in the Table below:

TABLE II

| Example # | Hydrocarbon Type | Fouling ($\Delta T$, °F.) |
| --- | --- | --- |
| 5 | Crude (BT) | 59 |
| 6 | Crude (BT) Distillate | 0 |
| 7 | Asphaltenated Crude Oil (BT) | 70 |
| 8 | SJF Crude | 0 |

TABLE II-continued

| Example # | Hydrocarbon Type | Fouling (Δ T, °F.) |
|---|---|---|
| 9 | Coastal Crude | 20 |
| 10 | Deasphaltenated Crude (BT) | 10 |

The Thermal Fouling Tester results presented in the above table gives the fouling characteristics of the various hydrocarbon streams. The data of Table II is seen to confirm the fouling tendencies or lack thereof of various hydrocarbon streams as predicted by the method of this invention. The left chromatogram of FIG. 1 predicted the heavy fouling property of Crude (BT) as shown by Example 5. Similar Examples 8 and 9 show the validity of the chromatograms of FIG. 3 in predicting the low fouling tendencies of SJV and Coastal Crudes. Further, Example 10 confirms the prediction from the right chromatogram of FIG. 4 of the low fouling tendency of the Deasphaltenated Crude (BT).

It will be further understood that the present invention is not necessarily limited to the above-described embodiments, but rather is subject to variations and modifications without departing from its broader aspects.

What is claimed is:

1. A method for determining the tendency of a liquid hydrocarbon stream to foul equipment comprising the steps of:
   (a) depositing a sample of liquid hydrocarbon from a liquid hydrocarbon stream onto a surface of a thin film made up of a chromatographic separation material;
   (b) letting the sample of liquid hydrocarbon migrate radially outward within said film for sufficient time so that hydrocarbon compatible fractions in the same separate from any hydrocarbon-incompatible asphaltenes in the sample, wherein said hydrocarbon compatible fractions form a matrix portion in the film and any hydrocarbon-incompatible fractions form a dark ring within the matrix portion and wherein any ring formed is disposed within a central region of the matrix portion and is distinguished from the matrix portion by a dark area having a boundary with respect to a lighter area; and
   (c) determining the tendency of the liquid hydrocarbon stream to foul equipment by comparing the matrix portion with any dark ring formed from any hydrocarbon-incompatible asphaltenes in the sample, wherein the area and intensity of any ring formed in relation to the matrix portion provides an indication of the tendency of the liquid hydrocarbon stream to foul equipment.

2. The method according to claim 1, wherein the chromatographic separation material is such that hydrocarbon compatible fractions and any hydrocarbon-incompatible asphaltenes in said sample separate from the sample in step (b) by adsorption.

3. The method according to claim 1, wherein the sample of liquid hydrocarbon is admixed with an amount of a paraffinic solvent prior to step (a).

4. The method according to claim 3, wherein the amount of solvent admixed with the sample is from 1 to 3,000 percent by weight based on the weight of the sample.

5. The method according to claim 1, wherein the chromatographic separation material is selected from the group consisting of acidic silica gel, alumina, and kieselguhr.

6. The method according to claim 5, wherein the chromatographic separation material is acidic silica gel.

7. A method for reducing the fouling tendency of a hydrocarbon stream flowing through a vessel comprising the steps of:
   (a) carrying out the method of claim 1; and
   (b) based on the determination of the tendency of the liquid hydrocarbon stream to foul equipment and in response thereto, adding at least an antifouling amount of an antifouling agent to said stream to reduce its tendency to foul.

* * * * *